(12) United States Patent
Patel et al.

(10) Patent No.: US 9,126,059 B2
(45) Date of Patent: Sep. 8, 2015

(54) SUNSCREEN COMPOSITIONS

(75) Inventors: Bhalchandra Somabhai Patel, Glen Allen, VA (US); Jay Roberts Dickerson, Midlothian, VA (US); Gary Robert Agisim, Henrico, VA (US); Richard John Kenny, Glen Allen, VA (US)

(73) Assignee: Wyeth LLC, New York, NY (US)

( * ) Notice: Subject to any disclaimer, the term of this patent is extended or adjusted under 35 U.S.C. 154(b) by 2 days.

(21) Appl. No.: 12/902,802

(22) Filed: Oct. 12, 2010

(65) Prior Publication Data

US 2011/0085994 A1    Apr. 14, 2011

Related U.S. Application Data

(60) Provisional application No. 61/250,615, filed on Oct. 12, 2009.

(51) Int. Cl.
*A61K 8/00* (2006.01)
*A61Q 17/04* (2006.01)
*A61K 8/02* (2006.01)
*A61K 8/60* (2006.01)
*A61Q 19/00* (2006.01)

(52) U.S. Cl.
CPC .............. *A61Q 17/04* (2013.01); *A61K 8/0229* (2013.01); *A61K 8/60* (2013.01); *A61Q 19/001* (2013.01)

(58) Field of Classification Search
None
See application file for complete search history.

(56) References Cited

U.S. PATENT DOCUMENTS

| 6,231,838 | B1 | 5/2001 | Morefield et al. |
| 7,473,707 | B1 | 1/2009 | O'Lenick et al. |
| 7,569,607 | B2 | 8/2009 | O'Lenick et al. |
| 7,858,075 | B2 | 12/2010 | O'Lenick et al. |
| 2008/0286217 | A1 * | 11/2008 | Chaudhuri ............. 424/59 |
| 2008/0305059 | A1 * | 12/2008 | Chaudhuri ............. 424/62 |
| 2008/0319069 | A1 | 12/2008 | O'Lenick et al. |
| 2009/0170943 | A1 | 7/2009 | O'Lenick et al. |
| 2009/0171057 | A1 | 7/2009 | O'Lenick et al. |
| 2009/0253812 | A1 | 10/2009 | O'Lenick et al. |

FOREIGN PATENT DOCUMENTS

| JP | 2003212720 | 7/2003 |
| JP | 2006335654 | 12/2006 |

OTHER PUBLICATIONS

Federal Register 21 CFR Parts 347 and 352, Sunscreen Drug Products for Over-the-Counter Human Use; Proposed Amendment of Final Monograph; Proposed Rule Federal Register, vol. 72, No. 165, Aug. 27, 2007.
2005 Brochure pertaining to Spider Esters from SurfaTech Corporation located in Lawrenceville, Georgia.
2007.1 Brochure pertaining to Spider Esters from SurfaTech Corporation located in Lawrenceville, Georgia.
2007.2 Brochure pertaining to Spider Esters from SurfaTech Corporation located in Lawrenceville, Georgia.
"Spider Esters; A New Class of Polar Esters", (Presentation) SurfaTech Corporation located in Lawrenceville, Georgia, Nov. 7, 2005.
"Spider Esters; A New Class of Polar Esters," (Presentation) SurfaTech Corporation located in Lawrenceville, Georgia, 2007.
"Spider Ester ESO Lip Balm with SPF & Vitamins," (Formulation Data Sheet) SurfaTech Corporation located in Lawrenceville, Georgia, Jul. 4, 2005.
"Spider Ester GEC Sunscreen Stick," (Formulation Data Sheet) SurfaTech Corporation located in Lawrenceville, Georgia, Jul. 4, 2005.

* cited by examiner

*Primary Examiner* — Lezah Roberts
*Assistant Examiner* — Nannette Holloman
(74) *Attorney, Agent, or Firm* — Maureen P. O'Brien; Joseph F. Reidy; Jeffrey M. Gold

(57) ABSTRACT

The present invention provides a taste-masked sunscreen composition comprising at least one sunscreen and a spider ester wherein the sunscreen and the spider ester are in intimate association. A method of making the taste-masked sunscreen composition is provided.

1 Claim, 1 Drawing Sheet

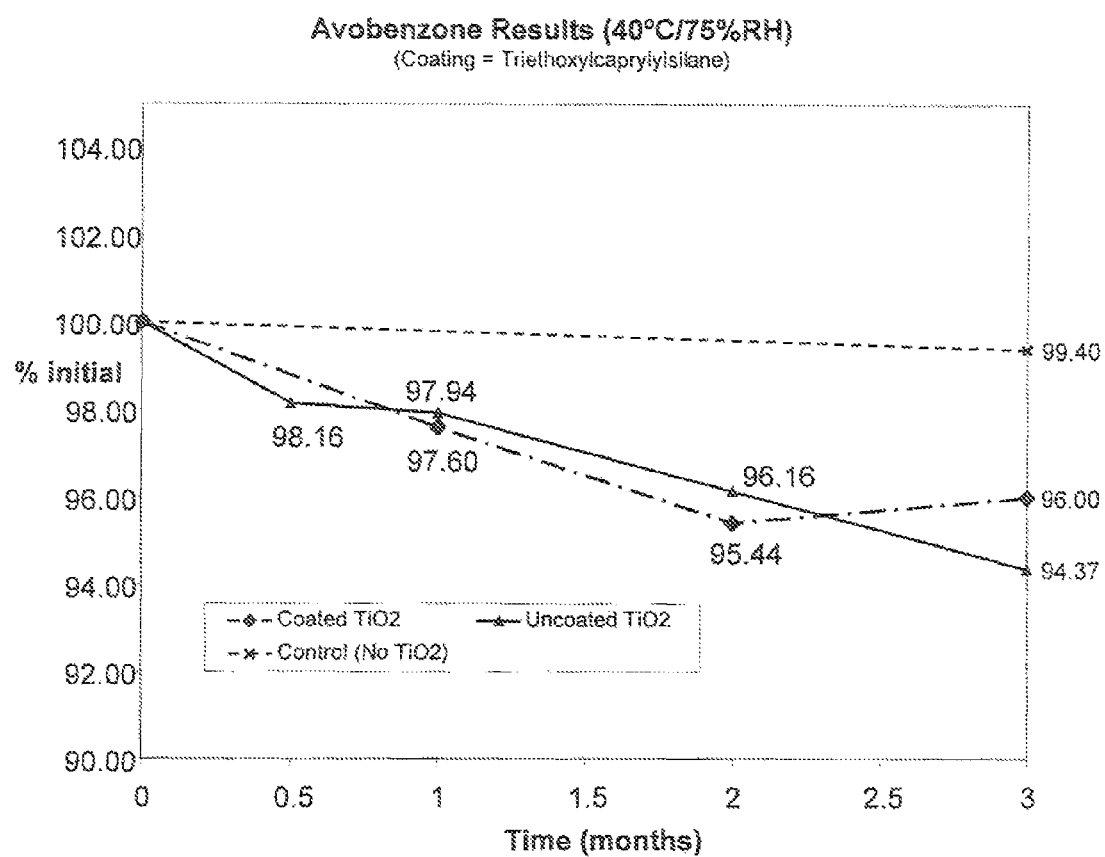

SUNSCREEN COMPOSITIONS

This application claims priority from U.S. Provisional Application 61/250,615 filed Oct. 12, 2009 entitled, "Sunscreen Compositions," the content of which is incorporated herein in its entirety to the extent that it is consistent with this invention and application.

FIELD

The invention relates to new and useful taste-masked lip treatment compositions and methods of making the compositions. The lip treatment compositions of the inventions comprise efficacious amounts of UVA and UVB sunscreens in which organic sunscreen components are efficaciously taste-masked.

BACKGROUND

Human lips are prone to sun damage when exposed to UVA and/or UVB radiation. Efficacious protection from UVA and UVB radiation requires the use of significant amounts of sunscreen and often a mixture of organic sunscreens to achieve efficacious protection from both UVA and UVB radiation. UVB, which is radiation in the wavelength range of 290 nm-320 nm, has been characterized traditionally as the sunburn radiation as it is the radiation that typically produces redness of the skin. In addition to producing redness, it can decrease enzymatic and non-enzymatic antioxidants in the skin and impair the natural protective mechanisms in the skin contributing to DNA damage and potential skin cancer. The dangers of UVA radiation, which is radiation in the wavelength range of 320 nm to 400 nm, have only recently been recognized. Chronic exposure to UVA radiation can cause damage to gene P53 DNA, possibly leading to cancer. Additionally, the longer UVA wavelengths allow for relatively deep penetration into the skin tissues causing damage to the elastic fibers and collagen which give skin its shape, thus causing wrinkling and eventually premature skin aging. Thus, protecting the skin including the skin of the lips from UBA and UVB is important to maintenance of skin health and appearance.

Unfortunately, sunscreens, particularly organic sunscreens, have a bad taste. Some sunscreens including avobenzone which is particularly useful for UVA protection have a very bad taste. This bad taste is not an issue for lotions that are applied to the body to protect body surfaces from the sun damage, but become a significant problem when sunscreens are incorporated into lip treatment compositions. Unfortunately, there are no other available sunscreens which afford UVA protection as effectively as avobenzone.

Prior to the present invention, forming a lip balm or treatment with levels of sunscreen that that would have an efficacy of SPF 30 or greater (i.e., significant UVB protection) has yielded compositions that have a very unpleasant taste. The taste is sufficiently unpleasant to discourage use and/or result in limited compliance. Commercial lip products with SPF 30 or greater protection claims are widely recognized to be bad tasting. The addition of avobenzone to such compositions to provide UVA protection exacerbates the problem significantly.

Conventionally, sweeteners and/or flavorants have been used to cover or mask unpleasant tastes. In this approach, the sweetener and/or flavorant competes with the undesirable taste. While this may be successful in some applications, it is not satisfactory for masking the taste of the very strong and/or bitter flavors of organic sunscreens. Additionally, the flavor and/or sweetener may lack the persistence of taste over the entire time frame that the sunscreen remains on the lips, resulting in the evolution of a distasteful sensation after a period of time.

Coatings and forms of encapsulation are other approaches for taste-masking. However, coatings and/or encapsulation may alter the reactivity or release of the active agent. Further, coating or encapsulation of a bad tasting material in a lip product is typically an even more difficult problem than taste-masking of an ingested material, as unlike ingested materials, the product is intended to stay on the lips for a period of several hours. The integrity of the coating upon the lips must be maintained for a period of several minutes to several hours. The integrity of the coating upon exposure air, moisture and or light must be maintained over a period of many times longer than the period of time needed to swallow an ingestible composition.

In addition to the need to maintain taste-masking over a long period of use, in the case of the sunscreen in a lip balm, the taste-masking mechanism should not impair the sunscreen's function of protecting the lip tissue from UVA and/or UVB radiation.

SUMMARY

The invention provides a taste-masked sunscreen composition comprising at least one sunscreen and a spider ester wherein the sunscreen and the spider ester are in intimate association. In one exemplary embodiment, the sunscreen is an organic sunscreen. Avobenzone is exemplary of an organic sunscreen. In one exemplary embodiment the spider ester is selected from the group consisting of spider esters having a common linking group selected from glycerol, glycol, sorbitol and combinations thereof.

In one exemplary embodiment of the taste-masked sunscreen composition, the ratio of the total amount of sunscreen to spider ester is about 0.6 to about 2 by weight. Optionally, the taste-masked sunscreen composition may further comprise a photostabilizer.

The invention provides a lip treatment comprising a taste-masked sunscreen composition wherein the taste-masked sunscreen composition comprises at least one sunscreen and a spider ester and wherein the sunscreen and the spider ester are in intimate association. In one exemplary embodiment, the lip treatment is an extensible and retractable lip balm stick.

The invention provides a method of taste-masking a sunscreen composition. The method comprises combining at least one sunscreen with a spider ester in an intimate association. In one embodiment the method comprises combining the sunscreen with the spider ester and optionally a photostabilizer prior to combination with any additional ingredients.

In one embodiment a method of making a stick lip balm is provided. The method comprises combining a taste-masked composition comprising at least one sunscreen and a spider ester in an intimate association with at least one melted structurant wax.

DETAILED DESCRIPTION

The present invention is directed both to lip treatments including lip balms with efficacious amounts of organic sunscreens in which the organic sunscreen is taste-masked, and to a taste-masking method for sunscreens. In a preferred embodiment the lip treatment is a lip balm in a stick presentation. The taste-masked sunscreens of the invention comprise at least one sunscreen having unpleasant organoleptic properties and one or more spider esters.

The term "unpleasant organoleptic properties" as used herein means a taste and/or odor associated with a composition that a reasonable user of the composition would find to be unpleasant upon contact with the mouth and or lip area and/or upon ingestion. Taste may include such true tastes as bitter and/or sour for example and/or alternatively an odor and/or flavor that imparts an unpleasant organoleptic response due to contact with the lip or mouth area.

The term "effective amount" of a sunscreen is an amount of sunscreen sufficient to provide measurable protection from solar radiation as determined by having a measurable SPF (Sun Protection Factor) value and/or UVA protection value.

The term "SPF" (Sun Protection Factor) means the UVB energy required to produce a minimal erythema dose on sunscreen treated skin divided by the UVB energy required to produce a minimal erythema dose on unprotected skin.

The term "spider ester" means a compound comprised of fatty acid groups esterified to short polyoxalkylene chains which in turn are attached to a common linking group as described, for instance, in U.S. Pat. No. 7,473,707 incorporated herein by reference.

The term "effective amount of a spider ester" as provided herein is defined as an amount of the spider ester at least sufficient to provide taste-masking of an organic sunscreen or a combination of organic sunscreens when contacted by the lip or mouth areas. In preferred embodiments the taste-masking is sufficient to effect essentially complete taste-masking of the unpleasant taste of the active. However, it is recognized that reduction of the degree of unpleasant taste may be suitable in some applications. Accordingly, sufficient amount of spider ester to reduce unpleasant taste or alternatively improve taste should be considered within the scope of "effective amount" of spider ester.

As used herein a "lip treatment" is a semisolid composition for application to the lips that provides protective and/or moisturizing properties, end/or a beneficial agent and or a sunscreen and/or pharmaceutical active to the lip or mouth area. These compositions include lip balms in a stick presentation as well as soft lip balms such as, for example, those dispensed in jars, pots or tubes.

The term "stick lip balm" means a lip balm with sufficient structurant that it can be formed into a stick that is extensible and retractable from a container and is sufficiently robust to substantially retain the stick shape under typical commercial conditions of shipping, storage and use.

The term "lipstick" means is a waxy stick product containing pigment wherein the pigment is transferable to the lips to impart a visible color to the lips. Lipsticks may be cosmetics or lip treatments. Lipstick is a lip treatment if in addition to imparting color it provides protective and/or moisturizing properties, and/or a beneficial agent and or a sunscreen and/or a pharmaceutical active to the lip or lip area.

The term "organic sunscreen" means a compound or mixture of compounds that can protect human skin from UVA and/or UVB radiation and is the class of compounds classified by those skilled in the art of chemistry as organic chemicals. Exemplary organic sunscreens include, but are not limited to, aminobenzoic acid, avobenzone, cinotate, homosalate, meradimate, octocrylene, oxybenzone, octinoxate, octisalate, padimate O, ensulizole, sulisobenzone and trolamine salicylate.

The term "inorganic sunscreen" means a compound or mixture of compounds that can protect human skin from UVA and/or UVB radiation and is the class of compounds classified by those skilled in the art of chemistry as inorganic chemicals. Exemplary inorganic sunscreens include, but are not limited to, zinc oxide and titanium dioxide.

The terms "about" or "approximately" mean within an acceptable range for the particular parameter specified as determined by one of ordinary skill in the art, which will depend, in part, on how the value is measured or determined, i.e., the limitations of the measurement system. For example, "about" can mean a range of up to 10% of a given value.

"Percent" or "%" as used herein refers to the percentage by weight of the total composition, unless otherwise specified.

The term "wt/wt", unless otherwise indicated, means weight of a given component or specified combination of components to total weight of the composition expressed as a percentage.

A designation that a substance is a semisolid, should be taken to mean the physical state of the substance in the temperature range of about 20° C. to about 40° C.

The term "petrolatum" refers to petroleum jelly, which is a mixture of the softer members of the paraffin or methane series of hydrocarbons, obtained from petroleum as an intermediate product in the distillation. Petrolatum is typically perceived as soothing when applied to the human skin.

In a preferred embodiment, the organic sunscreen(s) in the lip treatment compositions of the present invention are taste-masked using spider esters. Taste-masking is achieved by forming an intimate association between the organic sunscreen(s) and spider ester(s) and optionally, a photostabilizer, prior to combining the intimately associated sunscreen and spider ester and optionally photostabilizer with other components of the composition.

Spider esters have been described and claimed for cosmetic use as emollients in U.S. Pat. No. 7,473,707 and U.S. Published Applications Numbers 2008/0319069, 2009/0171057, and 2009/0170943 for use in moisturization and emolliency for the skin and are incorporated herein by reference. The so-called "spider esters" have a fatty acid group connected through a short polyoxyalkylene to a common linkage group. The resulting ester has a three-dimensional molecular structure with the general configuration that resembles a spider, with the linkage group forming "the body" of the "spider", the low number polyalkenyl groups forming the first portion of the "spider legs" connecting the body and the fatty acid ester groups forming the remainder of the "spider". The combination of the common linking group and the short polyoxyalkylene chains creates a three dimensional structure with limited rotation. However, it is believed, without wishing to be held to the belief, that is does not form a closed structure such as a cage in the conventional sense as the fatty acid esters are believed to extend from the structure. Further, Spider esters have the unusual feature of lacking surfactant properties even though the building blocks of the spider esters are common building blocks in surfactants. This lack of surfactant properties is believed to be due to the stearic hindrance in the molecular structure.

Spider esters having particular utility for taste-masking are spider esters having a common linking group selected from glycerol, glycol or sorbitol with short chain of ethylene oxide units, short chain of propylene oxide units or a mixture thereof attached to each oxygen of the linking group. The polyoxyalkene chain attached to each oxygen preferably has from 1-5 polyoxyalkene units. The fatty acid esters esterified to the polyoxalkene chains typically have alkyl chains of from 7-21 carbon atoms. In one embodiment, spider esters having the common linking group of sorbitol are preferred. Spider esters having glycerol, glycol and sorbitol linking groups are commercially available and/or may be prepared in accordance with U.S. Pat. No. 7,473,707.

In one exemplary embodiment, taste-masking of organic sunscreen(s) with spider ester having sorbitol as the common linking group, taste-masking was achieved using about 1:1+/−10% by weight of the total amount of sunscreen and the spider ester. More generally, the ratio of amount of sunscreen to the amount of spider ester may range from about 0.6 to about 2; alternatively from about 0.85 to about 1.3; and alternatively from about 0.85 to about 1.20 by weight. Without wishing to be held to the theory, it is believed that these ratios are the minimum ratios needed to achieve taste-masking, however, larger amounts of spider ester can be used without compromising the taste-making, for example spider ester to sunscreen ratios of about 10:1, alternatively about 20:1, alternatively 30:1, alternatively 40:1 and alternatively 50:1 may be used. It is believed the taste-masked sunscreen(s) of the present invention are resultant from the physical combination of the sunscreen(s) in intimate association with at least one spider ester.

Optionally, this intimate association between the sunscreen(s) and spider esters may be formed in the presence of a photostabilizer such as, for example, diethylhexyl 2,6-naphthalate. Use of a photostabilizer may be desirable if a the formulation includes a sunscreen(s) such as avobenzone which is susceptible to degradation. Representative photostabilizers include diethylhexyl 2,6-naphthalate, octocrylene, ethylhexyl methoxycrylene, 4-methylbenzylidene camphor, bemotrizinol, bisoctrizole, butyloctyl salicylate, hexadecyl benzoate, butyloctyl benzoate, terephthalylidene dicamphor sulfonic acid and diethylhexyl syringylidene malonate. The above list is not an exhaustive list of photostabilizers and those of skill in the art may consider the use of other photostabilizers. A photostabilizer may be used in an amount of about 0.1% to about 5%, alternatively about 0.1 to 2% and alternatively from about 0.1% to about 1% of the total lip balm composition.

The formation of an intimate association between the sunscreen and the spider ester is a critical factor in achieving taste-masking. The spider ester should be mixed with the sunscreen(s) to be taste-masked prior to combining the sunscreen and spider ester with other components. Mixing of the spider ester and the sunscreen to be taste-masked provides for the formation of an intimate association between the spider ester and the sunscreen(s) to be taste-masked. The term "intimate association" is used as the spider ester and the sunscreen from a stable interaction or "complex" which is stable at ambient temperatures but can be separated when heated to temperature above 100° C. In some embodiments, it is desirable to warm the spider ester—sunscreen mixture to facilitate the formation of the intimate relationship between the sunscreen and the spider ester. In an exemplary embodiment, the spider ester and the sunscreen are mixed together and heated to about 40° C. to about 80° C. for about 30 minutes to about 2 hours with stirring. This premixing of the spider ester and the sunscreen, preferably in the presence of warming, is required to achieve taste masking i.e., the mere presence of a spider ester and a sunscreen in a composition does not provide taste-masking of the sunscreen. Optionally, a photostabilizer may be included in this premix to inhibit degradation of the sunscreen.

While spider esters have an ability to taste-mask, the degree of taste-masking may vary depending on the spider ester used and/or the sunscreen to be taste-masked. For example, in an exemplary embodiment, two identical organic sunscreen mixtures were placed in intimate contact with two different spider esters in an amount of about a 1:1 ratio by weight. One sample of the sunscreen mixture was placed in contact with a glycerol-based spider ester and the other was placed in contact with a sorbitol-based spider ester and each mixture was heated to about 40° C. to about 50° C. for about 30 minutes with stirring. The thus treated sunscreens were then incorporated into two identical lip balm compositions. In the exemplary test compositions, the offensive taste of the organic sunscreens was essentially totally masked in the composition with the sorbitol-based spider ester, while the composition with the glycerol-based spider ester was improved over a composition that lacked a spider ester associated with a sunscreen, but less than that for the composition with the sorbitol-based spider ester. Taste-masking was determined by sensory testing methods commonly used by those skilled in the art. i.e., application of the composition to be tested to the lips of human subjects with human subjects to provide evaluation.

Representative organic sunscreens useful in the practice of the invention (with maximum suitable amounts of each sunscreen in % wt/wt listed following the sunscreen), include but are not limited to, amino benzoic acid (about 15%), avobenzone (about 3%), cinoxate (about 3%), octyl methoxycinnamate (about 10%), homosalate (about 15%), meradimate (about 5%), octocrylene (about 10%), octinoxate (about 7.5%), oxybenzone (about 6%), dioxybenzone (about 3%), padimate O (about 8%), ensulizole (about 4%), sulisobenzene (about 10%), trolamine salicylate (about 12%), benzophenone (about 10%), benzylidine compounds (about 6%), butyl methoxydibenzoylmethane (about 5%), bis-ethylhexyloxyphenol methoxyphenyl triazine (about 10%), camphor benzalkonium methosulfate (about 6%), diethyl amino hydroxy benzoyl hexyl benzoate (about 10%), diethylhexyl butamido trazoine (about 10%), disodium phenyl dibenzylmidazole tetrasulfonate (about 10%), drometrizole trisiloxane (about 15%), ethylhexyl dimethyl para-amino benzoic acid (about 8%), ethylhexyl methoxycinnamate (about 10%), ethylhexyl salicylate (about 5%), ethylhexyl triazone (about 5%), isoamyl p-methoxycinnamate (about 10%), 4-methylbenzylidene camphor (about 10%), methylene bis-benzotriazolyl tetramethylbutylphenol (about 10%), PEG-25 para-mainobenzoic acid (about 5%), phenylbenziamido methylbenzylidene camphor (about 6%) polysilicone-15 terephthalyidene dicamphor sulfonic acid (about 10%), bet, 2-glucopyranoxy propyl hydroxyl benzophenone (about 5%), butyl methoxydibenzoylmethane (about 10%), diisopropyl methyl cinnamate (about 10%), dimethoxyphenyl-[1-(3,4)-4,4-dimethyl]1,3 pentanedione (about 7%), ethylhexyl dimethyloxy benzylidene dioxoimidazoline propionate (about 3%), ferulic acid (about 10%), glyceryl ethylhexanoate dimethoxycinnamate (about 10%), glycerol para-aminobenzoic acid (about 10%), phenylbenzimidazole sulfonic acid (about 3%) and any combination of any of the foregoing. The above list is not an exhaustive list of organic sunscreens and those of skill in the art may consider the use of other organic sunscreens. The amounts listed in the preceding list are for each sunscreen individually. In some embodiments in which a plurality of sunscreens are used the total combined amount of an sunscreen should be less or equal to the sum of the maximum suitable amounts for each component sunscreen.

Although a single sunscreen may be use in a lip treatment composition, typically a combination of sunscreens will be used as each sunscreen has a characteristic wavelength range in which it affords protection and typically that range is less than the entire range for which protection is desired. Thus, use of a combination of sunscreens provides protection over a wider range of wavelengths. Additionally, efficacy of protection is also related to amount of sunscreen. As regulatory agencies limit the amount of each sunscreen compound that can be used, the use of multiple sunscreens may improve protection level while maintaining regulatory compliance.

Preferred organic sunscreens, their efficacious wavelength range and preferred amounts are as follows: amino benzoic acid, 260 nm-313 nm, about 5% to about 15%; padimate O, 290 nm-315 nm, about 1.4% to about 8%; dioxybenzone, 260 nm-380 nm, about 1% to about 3%; oxybenzone. 270 nm-350 nm, about 2% to about 6%; sulisobenzone, 260 nm-375 nm; about 5% to about 10%; cinoxate, 270 nm-328 nm, 1% to about 3%; octocrylene, 250 nm-360 nm, 7% to about 10%; avobenzone, 320 nm-400 nm, 1% to about 3%; octyl salicylate, 280 nm-320 nm, 3% to about 5%; homosalate, 295 nm-315 nm, 4% to about 15%; trolamine salicylate, 260 nm-320 nm, 5% to about 12%; octinoxate, 290 nm-320 nm, 2% to about 7.5%. In preferred embodiments, at least two sunscreens are used where the first sunscreen has an efficacious wavelength range that includes about 260 nm to about 300 nm and the second sunscreen has an efficacious wavelength range that includes about 320 nm to about 370 nm.

The use of avobenzone is particularly desirable for UVA protection as it is efficacious in the range of about 320 nm to 400 nm, a range in which most sunscreens provide limited to no protection. However, as noted hereinabove, avobenzone has particularly offensive organoleptic properties. Thus, prior to the present invention use of efficacious amounts of avobenzone in a lip treatment yielded a composition with such offensive taste that most humans would be quite reluctant to apply it to their lips In some lip balm embodiments it may be desirable to also include inorganic sunscreens such as titanium dioxide and/or zinc oxide, for example. Such compounds may be used in amounts of about 2% to about 25% wt/wt with higher amounts providing higher levels of protection. Unfortunately, although higher amounts of the inorganic oxides provide better protection, they typically also impart a thick layer of white material to the skin surface which is very undesirable on the lips. Thus for lip compositions, inorganic sunscreens are preferably used in amounts of less than about 15% wt/wt total amount of inorganic sunscreen; alternatively less than about 10%, and alternatively less than about 5%. To achieve the desired protection level, inorganic sunscreens are preferably used in combination with organic sunscreens in lip compositions to obtain efficacious protection.

A typical taste-masked lip treatment composition with sunscreens further comprises a wax or other pharmaceutically acceptable vehicle, emollients, oils and, optionally, one or more medicaments and/or other active agents and/or one or more beneficial agents.

Waxes and/or oils and/or semisolid hydrocarbon materials typically provide the lip protectant and/or occlusive properties associated with a lip treatment and/or lipbalm. Furthermore, the waxes and/or oils and/or semisolid hydrocarbon materials function as skin conditioning agents and skin protectants. Exemplary skin conditioning agents include hydrogenated poly(C6-14 olefin), isopropyl myristate, paraffin, beeswax, perfluorononyl dimethicone, Coenzyme Q10 formulations and Spilanthes acmella flower extract formulations. An exemplary skin protectant is dimethicone. Waxes also typically serve as structurants for stick lip balms permitting the stick to be extended and retracted in use while maintaining the stick form. Suitable waxes for stick compositions include animal waxes, plant waxes, mineral waxes, silicone waxes synthetic waxes and petroleum waxes. Exemplary specific waxes and amounts used include, but are not limited to, carnauba wax (about 0.1 to about 5%); paraffin wax (about 10 to about 40%); white wax (about 0.5 to about 10%); candelilla wax (about 0.1 to about 10%); beeswax (about 1% to about 50%), jojoba wax (about 0.1 to about 10%), ozokerite (about 0.1 to about 10%), polyethylene (about 0.1 to about 10%) and combinations thereof. The above list is not an exhaustive list of waxes, oils, semisolid hydrocarbon materials, skin conditioning agents and skin protectants and those of skill in the art may consider the use of other waxes, oils, semisolid hydrocarbon materials, skin conditioning agents and skin protectants.

In addition to providing protectant properties, oils and semisolid hydrocarbon materials may variously provide emolliency, solubilize other components, contribute to the organoleptic/sensory attributes such as lip feel, contribute to a glossy appearance, provide slip, and impact payoff in application, for example. Furthermore, oils and semisolid hydrocarbon materials function as skin conditioning agents and skin protectants and in some cases as viscosity increasing agents. Exemplary oils and semisolid materials that may be used in the present invention include, but are not limited to lanolin and lanolin derivatives, petrolatum, polyalphaolefins such as hydrogenated polydecene, arachidyl propionate, cetyl alcohol, isopropyl lanolate, isopropyl myristate, mineral oil, light mineral oil, octyldodecanol, oleyl alcohol, polybutene ethyl macadamiate, castor oil, jojoba ester oils, almond oil, oil of wheat germ, avocado oil, perhydrosqualene, hydrogenated castor oil, hydrogenated vegetable oil, cetyl ricinoleate, propylene glycol, isopropyl palmitate, stearyl alcohol, botanical butters and volatile and non-volatile silicone oils; and any combination of any of the foregoing. Suitable silicone oils include, but are not limited to, polyphenylmethyl siloxane, dimethicones, cyclomethicones, fluorosilocones and any combination of any of the foregoing. The above list is not an exhaustive list of oils and semisolid hydrocarbon materials, skin conditioning agents, skin protectants and viscosity increasing agents, and those of skill in the art may consider the use of other waxes, oils, semisolid hydrocarbon materials, skin conditioning agents and skin protectants. The amount of a given oil and/or semisolid hydrocarbon materials is typically about 0.1% to about 40%, alternatively about 0.1% to about 25%, alternatively about 0.1% to about 5% with the total amount of such materials typically less than about 50% for a stick lip balm product.

In some embodiments, it is preferable that a portion of the oil be silicon oil as it facilitates persistence of the composition on the lips and provides for moisturization, a smooth feel and ease of spreading. Some silicon oils such as dimethicone, for example, also provide protectant properties. In an exemplary embodiment dimethicone may be used in an amount of about 0.15% to about 6%, alternatively about 1% to about 3.5% and alternatively about 1.5% to about 3.5%; and/or perfluronony1 dimethicone may be used in an amount of about 0.05 to about 6%, alternatively about 0.1% to about 5% and alternatively about 0.3% to about 5%. In some embodiments in which dimethicone and/or flurosilicone are used it is desirable to mix them with a solubilizing agent such as hydrogenated polydecene prior to combining them with other waxes and oils.

The composition may further comprise moisturizing oils. Exemplary moisturizing oils suitable for use in the composition included, but are not limited to, sunflower oil, coconut oil, castor oil, vegetable oil, corn oil, aloe vera oil, canola oil, soybean oil, jojoba oil, olive oil, babassu oil, avocado oil, apricot oil, meadowfoam seed oil, macadamia seed oil, oat kernel oil, palm seed oil, safflower oil, sandalwood oil, sesame oil, almond oil, wheat germ oil, cranberry oil and combinations thereof. The above list is not an exhaustive list of moisturizing oils and those of skill in the art may consider the use of other moisturizing oils. Oils may be included in the composition in amounts of about 1% to about 65%.

Optionally, the lip treatment composition may further comprise one or more antioxidants. Antioxidants may protect the composition from oxidation (e.g. becoming rancid) and/or provide lip conditioning benefits upon application to the lips. Tocopherols, tocopheryl acetate, some botanical butters and green tea extracts are exemplary natural product antioxidants suitable for use in the composition. Other suitable antioxidants include propyl octyl and dodecyl esters of gallic acid, butylated hydroxyanisole, butylated hydroxyltoluene, nordihydro guaiaretic acid. A single antioxidant may be used or a combination of two or more antioxidants. The above list is not an exhaustive list of antioxidants and those of skill in the art may consider the use of other antioxidants. Typically total amount of antioxidant is less than about 4%, alternatively less than about 2%, and alternatively less than about 1%.

Optionally, the lip treatment composition may further comprise a compound that reduces the appearance of aging such, for example, at least temporarily making fine lines and/or wrinkles less visible. Organic compounds which reduce the appearance of aging include, but are not limited to, coenzyme Q, hyaluronic acid, hyaluronate salts and derivatives of hyaluronic acid, and spilanthes flower. Formulations of coenzyme Q is are commercially available. An example of a commercially available Coenzyme Q10 formulation contains Coenzyme Q10 (ubiquinone) (7.500%), dl-α-tocophery (acetate (Vitamin E) (20.000%) and alkyl benzoic acid ester (C12-15 alkyl benzoate) (72.500%). Formulations of hyaluronic acid, derivatives of hyaluronic acid and hyaluronate are commercially available. An example of a commercially available hyaluronic salt formulation contains ethylhexyl palmitate (95.300%), silican dimethyl silylate (2.500%), butylene glycol (1.000%), caprylyl glycol (0.500%), phenoxyethanol (0.350%), hexylene glycol (0.100%), sodium hyaluronate, low molecular weight (0.145%) and sodium hyaluronate, high molecular weight (0.055%). Formulations of the spilanthes flower are commercially available. An example of a commercially available spilanthes flower formulation contains caprylic/capric triglyceride (97.050%) and spilanthes acmella flower extract (2.950%). A single antioxidant may be used or a combination of two or more antioxidants. The above list is not an exhaustive list of organic compounds that reduce the appearance of aging and those of skill in the art may consider the use of other organic compounds that reduce the appearance of aging. Typically, the total amount of organic compounds that reduce the appearance of aging are less than about 4%, alternatively less than about 2%, and alternatively less than about 1%.

Inorganic compounds which reduce the appearance of aging typically do so by diffraction or light scattering. Exemplary inorganic compounds that reduce the appearance of aging include but are, not limited to colloidal silicon dioxide and fumed alumina. Typically total amount of inorganic compounds that reduce the appearance of aging are less than about 3%, alternatively less than about 2%, and alternatively less than about 1%.

Optionally, the lip treatment composition may further comprise a preservative. Suitable preservatives include parabens, mixtures of parabens, imidazolidinyl urea, diazolidinyl urea and mixtures thereof. The above list is not an exhaustive list of preservatives and those of skill in the art may consider the use of other preservatives. Total amount of preservative is preferably less than 1%, alternatively less than 0.5% and alternatively less than 0.2%.

Optionally, the lip treatment composition may further comprise a viscosity increasing agent to provide hardness and structural support useful in forming a stick comprised of the composition of the invention. Suitable viscosity increasing agents include carnauba wax, white wax, paraffin, candelilla wax, microcrystalline was, cetyl alcohol, steryl alcohol, ozokerite and mixtures thereof. The above list is not an exhaustive list of viscosity increasing agents and those of skill in the art may consider the use of other viscosity increasing agents. The total amount of viscosity increasing agents is about 0.1 to about 30% wt/wt of the composition.

Optionally, the composition may further comprise a flavorant. Flavorants are typically used in amounts of about 0.1% to 5%. Amounts may vary depending on the potency of the flavorant and matrix in which the flavorant is presented. Flavorants may be derived from natural products, synthesized flavorants or combinations thereof. The flavorant may be a single flavor or a combination of flavors. Flavorants are commercially available. An example of a commercially available flavorant is a grapefruit lime flavor which contains natural and artificial flavors (99.95%), medium chain triglycerides and Vitamin E (0.05%).

Optionally sweeteners such as sucralose, saccharine, aspartame, steva and combinations thereof may be included in the composition in amounts of about 0.01% to about 0.1%.

Optionally, the composition may further comprise medicaments including, but not limited to, menthol, camphor, eucalyptus, salicylic acid, allantoin, benzocaine, derivatives of salicylic acid, phenol and pramoxine. In some embodiments petrolatum and/or dimethicone may also provide medicament benefits. The above list is not an exhaustive list of medicaments and those of skill in the art may consider the use of other medicaments. Typically medicaments which are added for medicament purposes only will be added in amounts of less than about 3%. Amounts may vary depending on the potency of the medicament and the matrix in which the medicament is presented.

Optionally, colorant that imparts color to the composition and/or lips may be included in the composition. For a lip balm the colorant should not be of an amount, particle size, and/or presented in a matrix that would permit transfer of colorant that imparts a color to the lips during application. For a lipstick, a colorant that transfers to the lips and imparts color to the lips should be used. Colorants include, for example, natural colorants such as plant extracts, natural minerals, or carmine, synthesized and/or processed colorant materials such as iron oxides, synthetic dyes, organic compounds, lake colorants, and FDA certified colorants for use on the lips. The above list is not an exhaustive list of colorants and those of skill in the art may consider the use of other colorants. Formulations of colorants are commercially available. An example of a commercially available colorant contains caprylic/capric triglycerides (59.5%), titanium dioxide (39.6%), castor oil phosphate (0.5%) and triethoxycaprylylsilane (0.4%). The use of a colorant containing titanium dioxide can affect the stability of some sunscreens such as Avobenzone. It has been observed that colorants containing coated titanium dioxide can enhance the stability of Avobenzone. Optionally in some embodiments it may be desirable to include a color enhancer such as, for example, a pearlescent material.

Optionally, a sensate may be included in the composition. A sensate is a composition that initiates a sensory perception such as heating or cooling, for example, when contacted with the skin and/or lips. Exemplary sensates include, but are not limited to, mint extracts, cinnamon extract, and capsaicin. Preferably sensates are derived from natural sources. However, synthetic sensates are within the scope of this invention. Sensates typically have high potency and accordingly may yield significant impact at low levels. The above list is not an exhaustive list of sensates and those of skill in the art may consider the use of other sensates. Typically less than about 3%, alternatively less than about 2%, and alternatively less than about 1% sensate are used.

Other beneficial agents known to one skilled in the art may likewise optionally be included in the composition. Aloe extracts and natural organic acids are exemplary of other beneficial agents. Natural organic acids including α-hydroxy acids may act as exfoliants, for example. Lactic acid is an exemplary α-hydroxy acid.

In an exemplary manufacturing process, the spider ester and organic sunscreen(s) and optionally a photostabilizer are combined and allowed to form an intimate association prior to combination with other components of the lip treatment composition. The composition of the invention can be prepared by melting the waxes and adding the other components to the molten wax mixture with stirring. Typically, the ingredients are combined stepwise with sufficient heating to melt any solid materials and stirring to achieve complete mixing. The preformed intimate association of spider ester, organic sunscreen and optionally a photostabilizer is added to the molten wax mixture.

Upon combination of all ingredients the composition is transferred to a container. For soft lip balms, the composition is typically placed in a container that facilitates storage and removal of a soft material such as a jar, or pot or tube, for example. For stick lip balms, typically the molten composition is placed in a stick-forming container or containers and allowed to solidify. Optionally, once placed in the container, the forming stick may be subjected to a one or more heating and cooling cycles as it solidifies to optimize formation of the stick. In the case of the stick lip balm, the stick-forming container is the typically dispensing tube. In such a process, the molten composition contacts the walls of the container and once solidified the stick lip balm remains in contact with the walls of the container.

Alternatively, the molten composition may be filled into a mold and allowed to solidify in the mold to form a stick or bullet. Once formed, the stick/bullet is removed from the mold and placed in a dispensing container. The stick/bullet molding process is preferred for lipsticks as typical lipstick compositions are deformed in use if the molten lipstick composition is transferred directly to a stick forming container that also serves as a dispensing device. Lipstick compositions are typically more susceptible to deformation when touching the walls of the dispensing tube due to the high levels of oils typically used to disperse and transfer pigments.

An exemplary, suitable dispensing container for stick or bullets comprise an elevator portion which permits extending the stick from the dispensing container to facilitate application to the users lips and retraction of the stick back into the container for storage.

EXAMPLE 1

Taste-Masked Sunscreen Composition

An exemplary taste-masked sunscreen composition of a mixture of sunscreens in intimate association with a sorbitol spider ester and method for forming the intimate association compositions is provided. This composition and method are representative of the many compositions and methods that are within the scope of this invention. The exemplary embodiments are provided for illustrative purposes.

The inventors believe, without wishing to be held to the theory, that the order of mixing of certain of the components is directly related to the ability to achieve taste-masking. Namely, the spider ester and sunscreen(s) to be taste-masked and optionally a photostabilizer should be mixed together and allowed to form an intimate association prior to combination with other components of a lip treatment composition.

In one exemplary embodiment the spider ester material sorbeth-2-hexaoleate was warmed to about 50-55° C. and combined with the organic sunscreens to be taste-masked and a photostabilizer with stirring while maintaining the temperature to form the intimate relationship prior to combination with the other components. For the taste-masked sunscreen composition used in the lip treatment compositions of Tables 1, 2 and 3 of Example 2 the spider ester sorbeth-2-hexaoleate was combined with diethylhexyl 2,6-naphthalate (a photostabilizer), and a mixture of sunscreens including homosalate, octylsalate, oxybenzone, octinoxate and avobenzone prior to combining this mixture with the other components. More particularly in one exemplary embodiment, the sunscreens and photostabilizer were added sequentially to the heated spider ester with stirring continued after each addition and maintaining the temperature until the mixture was uniform. In one exemplary embodiment the sequence of addition was oxybenzone, octyl salicylic, avobenzone, homosalate, and diethyhexyl-2-naphthalate.

EXAMPLE 2

Taste-Masked Sunscreen Compositions

Exemplary compositions of stick lip balm composition with taste-masked sunscreens and enhanced functionality are provided in Tables 1, 2, 3 and 3A. Exemplary processes for making the compositions of Tables 1, 2, 3 and 3A and forming a stick lip balm are also provided. These compositions and methods are representative of the many compositions and methods that are within the scope of this invention. The exemplary embodiments are provided for illustrative purposes.

TABLE 1

| Ingredient | Amount % wt/wt |
| --- | --- |
| Hydrogenated polydecene | 4.71% |
| Paraffin wax | 20.00% |
| Isopropyl myristate | 1.00% |
| Perflurononyl dimethacone | 5.00% |
| Dimethicone | 3.00% |
| White wax | 2.00% |
| Carnauba wax | 1.00% |
| Methylparaben | 0.10% |
| Propylparaben | 0.06% |
| Cetyl Alcohol | 0.50% |
| Sucralose | 0.03% |
| Preformed Taste-Masked Composition | 54.0% |
| (Diethylhexyl 2,6-Naphthalate (photostabilizer) | 0.50%) |
| (Homosalate | 7.00%) |
| (Octylsalate | 5.00%) |
| (Oxybenzone | 5.00%) |
| (Octinoxate | 7.50%) |
| (Avobenzone | 3.00%) |
| (Sorbeth-2-hexaoleate (spider ester) | 26.10%) |
| Zinc oxide (50% in suspension) | 6.00% |
| Flavor | 1.50% |
| Vitamin E Acetate | 1.00% |

TABLE 2

| Ingredient | Amount % wt/wt |
| --- | --- |
| Hydrogenated polydecene | 9.47% |
| Paraffin wax | 20.00% |
| Isopropyl myristate | 1.00% |
| Perflurononyl dimethacone | 0.30% |

TABLE 2-continued

| Ingredient | Amount % wt/wt |
|---|---|
| Dimethicone | 1.50% |
| White wax | 2.00% |
| Carnauba wax | 1.00% |
| Methylparaben | 0.10% |
| Propylparaben | 0.06% |
| Cetyl Alcohol | 0.50% |
| Sucralose | 0.03% |
| Preformed Taste-Masked Composition | 53.0% |
| (Diethylhexyl 2,6-Naphthalate (photostabilizer) | 0.50%) |
| (Homosalate | 6.00%) |
| (Octylsalate | 4.50%) |
| (Oxybenzone | 5.00%) |
| (Octinoxate | 6.50%) |
| (Avobenzone | 3.00%) |
| (Sorbeth-2-hexaoleate (spider ester) | 25.0% |
| Zinc oxide (50% in suspension) | 6.00% |
| Colloidal silicon dioxide | 0.50% |
| Flavor | 2.94% |
| Vitamin E Acetate | 1.00% |
| Fumed Alumina | 0.30% |
| Sodium Hyaluronate formulation | 0.50% |
| Coenzyme Q-10 | 0.30% |
| *Spilanthes acmella* Flower Extract | 1.00% |
| Titanium Dioxide | 1.00% |

TABLE 3

Sunscreen composition containing uncoated Titanium Dioxide

| Ingredient | Amount % wt/wt |
|---|---|
| Dimethicone | 1.50% |
| Homosalate | 6.00% |
| Benzophenone-3 | 5.00% |
| Ethylhyexyl Salicylate | 4.50% |
| Butyl Methoxycinnamate | 3.00% |
| Ethylhexyl Methoxycinnamate | 6.50% |
| Diethylhexyl 2,6-Naphthalate | 0.50% |
| Sorbeth-2 Hexaoleate | 25.00% |
| *Copernicia Cerifera* | 1.00% |
| Cetyl Alcohol | 0.50% |
| Isopropyl Myristate | 1.00% |
| Hydrogenated Poly (C6-14) Olefin | 14.91% |
| Methylparaben | 0.10% |
| Propylparaben | 0.06% |
| Sucralose | 0.03% |
| Tocopheryl Acetate | 1.00% |
| Paraffin | 20.00% |
| Beeswax | 2.00% |
| Alumina | 0.30% |
| Perfluorononyl | 0.30% |
| Sodium hyaluronate formulation | 1.00% |
| Coenzyme Q10 | 0.30% |
| *Spilanthes acmella* flower extract | 1.00% |
| Colloidal Silicon Dioxide | 0.50% |
| Titanium Dioxide | 1.00% |
| Flavorant | 3.00% |

TABLE 3A

Sunscreen composition containing no Titanium Dioxide

| Ingredient | Amount % wt/wt |
|---|---|
| Dimethicone | 1.50% |
| Homosalate | 6.00% |
| Benzophenone-3 | 5.00% |
| Ethylhyexyl Salicylate | 4.50% |
| Butyl Methoxycinnamate | 3.00% |
| Ethylhexyl Methoxycinnamate | 6.50% |
| Diethylhexyl 2,6-Naphthalate | 0.500% |
| Sorbeth-2 Hexaoleate | 25.0% |
| *Copernicia Cerifera* | 1.00% |
| Cetyl Alcohol | 0.50% |
| Isopropyl Myristate | 1.00% |
| Hydrogenated Poly (C6-14) Olefin | 16.41% |
| Methylparaben | 0.100% |
| Propylparaben | 0.060% |
| Sucralose | 0.030% |
| Tocopheryl Acetate | 1.00% |
| Paraffin | 20.00% |
| Beeswax | 2.00% |
| Alumina | 0.300% |
| Perfluorononyl | 0.300% |
| Sodium hyaluronate formulation | 0.500% |
| Coenzyme Q10 | 0.300% |
| *Spilanthes acmella* flower extract | 1.00% |
| Colloidal Silicon Dioxide | 0.50% |
| Flavorant | 3.00% |

In an exemplary embodiment, the compositions of Tables 1, 2, 3 and 3A were prepared by combining the waxes including the white wax, carnauba wax, paraffin wax and cetyl alcohol and warming to 85-90° C. Once the waxes began to melt the mixture was stirred with a Lightnin Mixer. The methyl paraben and propyl paraben were dissolved in isopropyl myristate. The paraben myristate mixture was added to the melted waxes with continued stirring and the temperature was lowered to 70-75° C. The previously prepared spider ester-sunscreen composition as described in Example 1 was added to the molten wax mixture with stirring. All other ingredients except the sweetener (sucralose), Vitamin E acetate and inorganic components were combined and added to the wax mixture with stirring and maintaining the temperature at 70-75° C. For embodiments comprising coenzyme Q, the coenzyme Q should be heated to about 35-40° C. to dissolve solid particles. The Vitamin E acetate and sucralose may be added to the wax mixture and mixed until dispersed. Upon completion of the dispersion of the sucralose, any inorganic materials were added such inorganic materials included, for example, zinc oxide, titanium dioxide, fumed alumina and/or colloidal silicone dioxide.

The molten mixture thus formed was directly dispensed into dispensing tubes. Alternatively, the molten mixture may be dispensed into stick forming molds and cooled to solidify and then placed in dispensing tubes.

EXAMPLE 3

Taste-Masked Sunscreen Composition

An exemplary composition of a stick lip balm composition with taste-masking and an exemplary process for making the compositions is provided in Table 4 and the following paragraphs. This composition and method is representative of the many compositions and methods that are within the scope of this invention. The exemplary embodiments are provided for illustrative purposes.

TABLE 4

| Ingredient | Amount % wt/wt |
|---|---|
| Paraffin wax | 23.00% |
| Isopropyl myristate | 1.00% |
| White wax | 3.00% |
| Carnauba wax | 1.00% |
| Methylparaben | 0.10% |

TABLE 4-continued

| Ingredient | Amount % wt/wt |
| --- | --- |
| Propylparaben | 0.06% |
| Cetyl Alcohol | 0.50% |
| Saccharin | 0.03% |
| Preformed Taste-masked composition | 24.0% |
| (Oxybenzone | 3.50%) |
| (Octinoxate | 7.50%) |
| (Avobenzone | 3.00%) |
| (Sorbeth-2-hexaoleate (spider ester) | 10.00%) |
| Flavor/fragrance | 1.00% |
| White Petrolatum | 40.7% |
| Lanolin | 1.00% |
| Isopropyl Lanolate | 2.00% |
| Titanium Dioxide | 0.10% |

As indicated in Example 1, preferably the spider ester material is warmed to about 50-55° C. and combined with the organic sunscreens to be taste-masked with stirring while maintaining the temperature to form the intimate association prior to combination with the other components. Namely, for the composition of Table 4 the spider ester is combined with, oxybenzone, octinoxate, and avobenzone and allowed to form an intimate association prior to combining this mixture with the other components.

In an exemplary embodiment, the composition of Table 4 may be prepared by combining the waxes including the white wax, carnauba wax, paraffin wax and cetyl alcohol and warming to 85-90° C. Once the waxes begin to melt, the mixture should be stirred with, for example, a Lightnin Mixer. The methyl paraben and propyl paraben may be dissolved in isopropyl myristate. The paraben myristate mixture was added to the melted waxes with continued stirring and preferably the temperature is lowered to 70-75° C. The previously prepared spider ester-sunscreen composition is added to the molten wax mixture with stirring. The remainder of the components, except the saccharin, flavorant and inorganic material (e.g. titanium dioxide), may then be added with stirring and maintaining the temperature at 70-75° C. Upon completion of thorough mixing of the wax mixture, the saccharin, flavorant and inorganic material may be added.

The molten mixture thus formed may be directly dispensed into dispensing tubes, or alternatively, dispensed into stick forming molds and cooled to solidify and then placed in dispensing tubes.

EXAMPLE 4

Taste-Masked Sunscreen Composition

An exemplary composition of a soft lip balm composition with taste-masking is provided in Table 5. An exemplary process for making the composition of Table 5 and forming a soft lip balm is also provided. This composition and method is representative of the many compositions and methods that are within the scope of this invention. The exemplary embodiments are provided for illustrative purposes.

TABLE 5

| Ingredient | Amount % wt/wt |
| --- | --- |
| Petrolatum | 63.65% |
| Preformed Taste-masked-composition | 25.5% |
| (Oxybenzone | 3.50%) |
| (Octocrylene | 7.00%) |
| (Octyl methoxycinnamate | 7.50%) |
| (Sorbeth-2-hexaoleate (spider ester) | 17.50%) |

TABLE 5-continued

| Ingredient | Amount % wt/wt |
| --- | --- |
| Ascorbic Acid | 0.10% |
| Tocopherol Vitamin E | 0.25% |
| Grapefruit fragrance | 0.50% |

As indicated in Example 1, preferably the Spider Ester material is warmed to about 50-55° C. and combined with the organic sunscreens to be taste-masked with stirring while maintaining the temperature to form the intimate association prior to combination with the other components. Namely for the composition of Table 5 the spider ester is combined with, oxybenzone, octocrylene, octyl methoxycinnamate and allowed to form an intimate prior to combining this mixture with the other components.

An exemplary embodiment the composition of Table 5 may be prepared by warming the petrolatum sufficiently to melt. Once melted the taste-masked sunscreen composition and ascorbic acid may be added with stirring. Upon completion of thorough mixing of the petrolatum, taste-masked composition and ascorbic acid, the remaining ingredients may be added with stirring. As this composition is a soft lip treatment composition lacking structurant wax, it is preferably transferred to a container such as a pot, jar or tube while molten.

EXAMPLE 5

Taste-Masked Sunscreen Composition

Sunscreen Composition Containing Coated Titanium Dioxide

An exemplary composition of stick lip balm composition with taste-masked sunscreens and enhanced functionality is provided in Table 6. Exemplary processes for making the composition of Table 6 and forming a stick lip balm is given in Example 2. The composition and method are representative of the many compositions and methods that are within the scope of this invention. The exemplary embodiments are provided for illustrative purposes.

TABLE 6

| Ingredient | Amount % wt/wt |
| --- | --- |
| Dimethicone | 1.5% |
| Homosalate | 6.00% |
| Benzophenone-3 | 5.00% |
| Ethylhexyl salicylate | 4.5% |
| Butyl methoxycinnamate | 3.00% |
| Ethylhyexyl methoxycinnamate | 6.50% |
| Diethylhexyl 2,6-naphthalate | 0.55% |
| Sorbeth-hexaoleate | 25.0% |
| *Copernicia cerifera* | 1.00% |
| Cetyl alcohol | 0.500% |
| Isopropyl myristate | 1.00% |
| Hydrogenated poly (C6-14) Olefin | 14.91% |
| Methylparaben | 0.100% |
| Propylparaben | 0.060% |
| Sucralose | 0.030% |
| Tocopheryl acetate | 1.00% |
| Paraffin | 20% |
| Beeswax | 2.00% |
| Alumina | 0.300% |
| Perfluorononyl dimethicone | 0.300% |
| Sodium hyaluronate formulation | 0.500% |
| Coenzyme Q10 | 0.300% |
| *Spilanthes acmella* flower extract | 1.00% |
| Colloidal silicon dioxide | 0.50% |
| Colorant | 1.50% |
| Flavorant | 3.00% |

EXAMPLE 6

Sunscreen Evaluation

To confirm that UVA and UVB protection is maintained in the intimate association between the spider ester and the sunscreens, the stick lip balm of Table 2 was tested using in vitro testing.

UVA protection was determined using the UVA/UV Ratio of in vitro transmittance data method as set forth in the Federal Register Proposed Rule, of Star Ratings for UVA sun protection. This test procedure is based upon the method outlined in the Federal Register 21 CFR Parts 347 and 352, Sunscreen Drug Products for Over-the-Counter Human Use; Proposed amendment of Final Monograph; Proposed Rule Federal Register, Vol. 72, No. 165, Aug. 27, 2007.

The test is based on the assessment of UV-transmittance through a thin film of product sample spread on a roughened substrate, after exposure to a controlled dose of UV radiation. The product sample containing sunscreen is exposed to a radiation dose that is equivalent to ⅔ the SPF value times 20 mJ/cm$^2$. A UV radiation dose of 20 mJ/cm$^2$ is equal to one minimum erythema dose (MED). The calculated UVA-I/UV ratio is then used to classify the UVA protection offered by the test sample.

The SPF value (i.e. UVB protection value) is determined from the average percentage transmittance of the test material obtained from the 25 scans, 5 slides with 5 scans per slide. The average absorbance at each wavelength for the test material is recorded in a table and a chart is generated.

These test results showed that the Composition of Table 2 had an SPF value of 62 and a Star Rating of 2 out of a potential maximum of 4. Sensory testing with human subjects using conventional sensory panel testing methods confirmed good taste masking even in the presence of avobenzone.

EXAMPLE 7

Taste Evaluation

Organic sunscreens are well known to impart an unpleasant taste. Lip products containing organic sunscreens in a quantity and combination resulting in an SPF of 30, with no appreciable UVA screening, are widely recognized to taste bad.

Avobenzone, the only effective UVA organic sunscreen, has a very bad taste. Incorporation of UVA at the effective level of 3% results in a lip product that is extremely bad tasting, to the extent that reliable consumer compliance would not be attainable form commercial product. This observation was the motivation for searching for a composition and method for taste masking sunscreens.

Compositions containing Spider Ester ESO, representing the examples listed in Table I, were taste evaluated by a panel of five persons against lip compositions containing an identical sunscreen composition but with out the Spider Ester ESO. Both products featured SPF values of 50+ and effective UVA sunscreen activity. The products containing the Spider Ester ESO displayed excellent taste characteristics. The product without the Spider Ester ESO displayed an extremely bad taste, much worse than even commercial products of SPF 30 with no UVA sunscreen. The taste difference between the SPF 50+ (with 3% Avobenzone) compositions, with and without Spider Ester ESO, was very dramatic and unequivocal. The SPF 50+ (with 3% Avobenzone) composition, without the Spider Ester ESO, would not be commercially viable because of very bad taste, nor would this composition be a suitable candidate, or comparative, product for additional taste panel testing, again due very bad taste.

A lip product composition representing the example listed in Table I, with respect to composition and method of manufacture, was given to 20 persons. This composition represented a 50+ SPF, an effective UVA sunscreen (3% Avobenzone), and contained Spider Ester ESO. The 20 persons also received a commercial SPF 30 lip product with no effective UVA sunscreen. All twenty persons found that the Table I composition displayed an excellent taste. All twenty persons found that the commercial SPF 30 product was bad tasting. This result represents a unanimous preference for the more effective sunscreen lip product (SPF 50+ with effective UVA) with Spider Ester versus the less effective sunscreen product (SPF 30, no UVA).

EXAMPLE 8

Avobenzone Stability Study

For additional UVA efficacy, Avobenzone and titanium dioxide are a permitted combination per the proposed final sunscreen monograph. Unfortunately, transition metals, like titanium, can promote instability of the Avobenzone. A comparative study of the Avobenzone stability in the taste-masked sunscreen compositions of Table 3 and Table 6 was performed at 40° C. and 75% relative humidity to monitor the stability of Avobenzone in the composition of Table 6 which contains coated titanium dioxide versus the composition of Table 3 which contains uncoated titanium dioxide. The sunscreen composition of Table 3A contains no titanium dioxide and served as the control in the study. FIG. 1 shows that the stability of Avobenzone is improved in the presence of coated titanium dioxide. At the 3-month timepoint, 96.00% of the initial Avobenzone was measured in the presence of titanium dioxide coated with triethoxylccaprylylsilane, whereas, at the same timepoint, only 94.37% of the initial Avobenzone was measured in the presence of uncoated titanium dioxide. The data in FIG. 1 demonstrates that the use of coated titanium dioxide retards the degradation of Avobenzone that was observed with uncoated titanium dioxide.

Although the foregoing invention has been described in some detail by way of illustrations and examples for purposes of clarity of understanding, it will be obvious that certain changes and modifications may be practiced within the scope of the appended claims. Modifications of the above described modes of practicing the invention that are obvious to persons of skill in the art are intended to be included within the scope of the following claims.

What is claimed is:

1. A lip treatment formulation comprising a taste-masked sunscreen composition wherein the taste-masked sunscreen composition comprises:
    (a) about 25 wt % sorbeth-2-hexaoleate;
    (b) about 3 wt % avobenzone sunscreen;
    (c) about 0.5 wt % diethylhexyl 2,6-naphthalate;
    (d) at least one additional sunscreen;
    (e) wherein the ratio of the total amount of sunscreen to spider ester is from about 0.6 to about 2 by weight; and
    (f) wherein the sorbeth-2-hexaoleate, the avobenzone sunscreen, and the diethylhexyl 2,6-naphthalate are mixed together to form an intimate association prior to combining these ingredients with the other ingredients.

* * * * *